United States Patent [19]
Cox et al.

[11] Patent Number: 5,145,784
[45] Date of Patent: Sep. 8, 1992

[54] DOUBLE CAPTURE ASSAY METHOD EMPLOYING A CAPILLARY FLOW DEVICE

[75] Inventors: Daniel E. Cox, Franklin; Obsidiana Abril, Cambridge; Sara Bauminger, Newton; Bruce P. Neri, N. Andover; Lisa Shinefeld, Lexington, all of Mass.

[73] Assignee: Cambridge Biotech Corporation, Worcester, Mass.

[21] Appl. No.: 816,772

[22] Filed: Jan. 2, 1992

Related U.S. Application Data

[60] Continuation of Ser. No. 311,122, Feb. 14, 1989, abandoned, which is a division of Ser. No. 189,983, May 4, 1988, abandoned.

[51] Int. Cl.$^5$ .......................................... G01N 33/553
[52] U.S. Cl. .................................. 436/526; 436/523; 436/816; 436/901
[58] Field of Search ............... 436/523, 526, 816, 901

[56] References Cited

U.S. PATENT DOCUMENTS

| | | | |
|---|---|---|---|
| 4,115,535 | 9/1978 | Giaever | 424/1 |
| 4,141,687 | 2/1979 | Forrest et al. | 422/67 X |
| 4,279,617 | 7/1981 | Masson et al. | 422/57 X |
| 4,596,695 | 6/1986 | Cottingham | 422/58 |
| 4,710,472 | 12/1987 | Saur et al. | 435/287 |
| 4,745,075 | 5/1988 | Hadfield et al. | 436/523 |
| 4,837,168 | 6/1989 | de Jaeger et al. | 436/533 |
| 4,868,130 | 9/1989 | Hargreaves | 436/526 |

FOREIGN PATENT DOCUMENTS

WO86/04684  8/1986  World Int. Prop. O.
WO86/06493  11/1986  World Int. Prop. O.

*Primary Examiner*—Jill Johnston
*Attorney, Agent, or Firm*—Hamilton, Brook, Smith & Reynolds

[57] ABSTRACT

A capillary flow device useful in double capture assays, such as double capture immunoassays, and a double capture assay. The capillary flow device comprises a capillary track, a sample receptacle, a particle collecting means and, optionally, a magnet and a particle concentrator. The assay method is useful for determining any analyte of interest for which there is a specific binding partner.

23 Claims, 5 Drawing Sheets

DOUBLE CAPTURE ASSAY METHOD EMPLOYING A CAPILLARY FLOW DEVICE

This is a continuation of Ser. No. 07/311,122 filed on Feb. 14, 1989, now abandoned, which is a divisional of Ser. No. 07/189,983, filed on May 4, 1988 and now abandoned.

BACKGROUND

Assays which are based on binding between ligands or members of specific binding pairs are widely used to determine the presence and quantities of analytes of interest (e.g., chemical constituents or substances of a sample). Immunoassays, which are a type of ligand-binding assay, are based on the highly specific reaction which occurs between members of specific binding pairs: an antigen and its antibody (e.g., the antibody produced in response to presence of the antigen in a higher animal). In part because of this specificity, immunoassays are particularly useful in detecting analytes which occur in small quantities in a sample.

Agglutination immunoassays are one type of immunoassay and, as their name suggests, the immunochemical reaction which occurs results in clumping of particulates, such as red blood cells or particles to which reagents are bound.

Another often-used type of immunoassay is the radioimmunoassay, in which radioactively-labeled antigens are used as detectable reagents. In this case, the labeled antigen serves as a means of tracing and measuring the distribution of total antigen (labeled and unlabeled) between the antibody-bound and the antibody-free fractions. Quantities of labeled antigen and of antiserum are kept constant and the proportion of counts in the bound fraction is inversely related to the total quantity of antigen present.

Immunoradiometric assays are another form of immunoassay based on the use of radioactively-labeled selected antibodies. They differ from radio-immunoassay procedures in several ways. For example, fewer reactants are generally used, an excess quantity of labeled antibody is added so that all antigen in the standard or sample will be bound, separation of antibody in the bound fraction from antibody in the free fraction is required and there is a direct relationship between counts in the bound fraction and the total quantity of antigen present.

Separation of bound and free-fraction antigen or antibody is generally necessary in immunoassay techniques. For example, in radioimmunoassay procedures, precipitation of the antigen: antibody complex does not occur spontaneously because only small quantities (low concentrations) of reagents are used. Several methods of separating bound from free-fraction reagents have been developed. Pourfarzaneh, M. et al., *Methods of Biochemical Analysis*, 28:268-295 (1982). These are generally based on differences between the bound and the free fractions (e.g., physical, chemical, physicochemical, immunological differences) and may have limited applicability because, for example, they are time-consuming, complex or unable to effect complete separation of the two fractions.

An immunoassay method which is nonisotopic and makes it possible to separate the bound reagents from free-fraction reagents efficiently and easily would be very useful and would be particularly valuable if it also allowed easy detection and measurement of the separated phases.

SUMMARY OF THE INVENTION

The present invention relates to a capillary flow device useful for carrying out double capture ligand binding assay procedures, particularly double capture immunoassay procedures, and to a method of determining (i.e., detecting, identifying, quantitating and/or isolating) an analyte of interest in a sample, which is a double capture ligand binding procedure.

In particular, the present method is a double capture method in which two types of particles are used: one type, referred to as magnetic, is magnetically responsive (i.e., will respond in a magnetic field or when a magnetic force is applied and is not itself a magnet) and the other type is nonmagnetic (nonresponsive magnetically) and detectable. Both types of particles have attached to their surface ligand (e.g., antigen), specific binding partner for the ligand (e.g., antibody), or both. According to the method of the present invention, a sample to be analyzed for an analyte of interest, which can be any ligand for which a specific binding partner is available, is combined with both types of particles, free antibody where needed and, optionally, any buffers, salts and other reagents needed, to produce a reaction mixture. The reaction mixture is maintained or incubated under conditions appropriate for the ligand and its specific binding partner to bind, resulting in a mixture referred to as a reacted mixture. Magnetic particles (both agglutinated and nonagglutinated) are removed from the reacted mixture, at a defined location on the capillary track, by magnetic attraction, with the result that any particles remaining in the reacted mixture are nonmagnetic detectable nonagglutinated particles. The occurrence and/or number of nonmagnetic particles is subsequently determined, using known methods, and serves as an indication of presence/absence of the analyte of interest and/or as the basis for determining the quantity of analyte present. In the method of the present invention in which the quantity of analyte is determined, the number or volume of nonmagnetic particles recovered is determined and compared with a predetermined relationship (or standard) between the number or volume of nonmagnetic particles and the quantity of analyte of interest.

In one embodiment of the present invention, the analyte of interest is an antigen or an antibody and the method used is a double capture immunoassay method. In this embodiment, magnetic particles and nonmagnetic detectable particles which have antigen and/or antibody affixed to their surfaces are combined with the sample to be analyzed, free antibody if required and any necessary buffers, salts and other reagents. After incubation for sufficient time and under appropriate conditions (e.g., sufficient energy or force to cause the particles to move so that they collide and can interact and bind) for antigen and specific antibody to bind, magnetic particles (both agglutinated and nonagglutinated) are removed. The presence or absence and/or quantity of nonmagnetic detectable particles is subsequently determined and the presence or absence and/or quantity of antigen or antibody of interest in the sample is determined. In one embodiment, the nonmagnetic detectable particles are colored latex particles and, after the magnetic particles have been removed from the reacted mixture, the nonmagnetic detectable particles remaining are concentrated (e.g., by being captured on a porous material). Presence or absence and/or quantity of nonmagnetic colored particles is then determined visually.

The method of the present invention has several advantages over presently-available immunoassay methods. For example, the reaction can be carried out quickly, does not require radiolabeled or enzyme labeled reagents and can be visualized easily without the need for complex instruments. In addition, neither a washing step nor handling of reagents is necessary to separate the bound from the free phase.

The capillary flow device of the present invention is useful in carrying out the method of the present invention and can be used for carrying out other assay procedures which are double capture methods. The device comprises a sample receptacle located at one end of a capillary track, through which the sample/particle combination referred to as the mixture flows, and a means for collecting the nonmagnetic detectable particles, located at or close to the other end of the capillary track (i.e., the end opposite that at which the sample receptacle is located). The device can additionally comprise a magnet, for separating magnetic from nonmagnetic particles, which is located between the sample receptacle and the collecting means. In one embodiment, the collecting means comprises a means for separating the nonmagnetic detectable particles from the liquid. In one embodiment, it comprises a porous solid material, through which the liquid passes, and a liquid reservoir. The nonmagnetic detectable particles are, thus, concentrated, making them easily detected visually.

BRIEF DESCRIPTION OF THE DRAWINGS

FIG. 2 is a schematic representation of the method of the present invention.

DETAILED DESCRIPTION OF THE INVENTION

Figure 1:
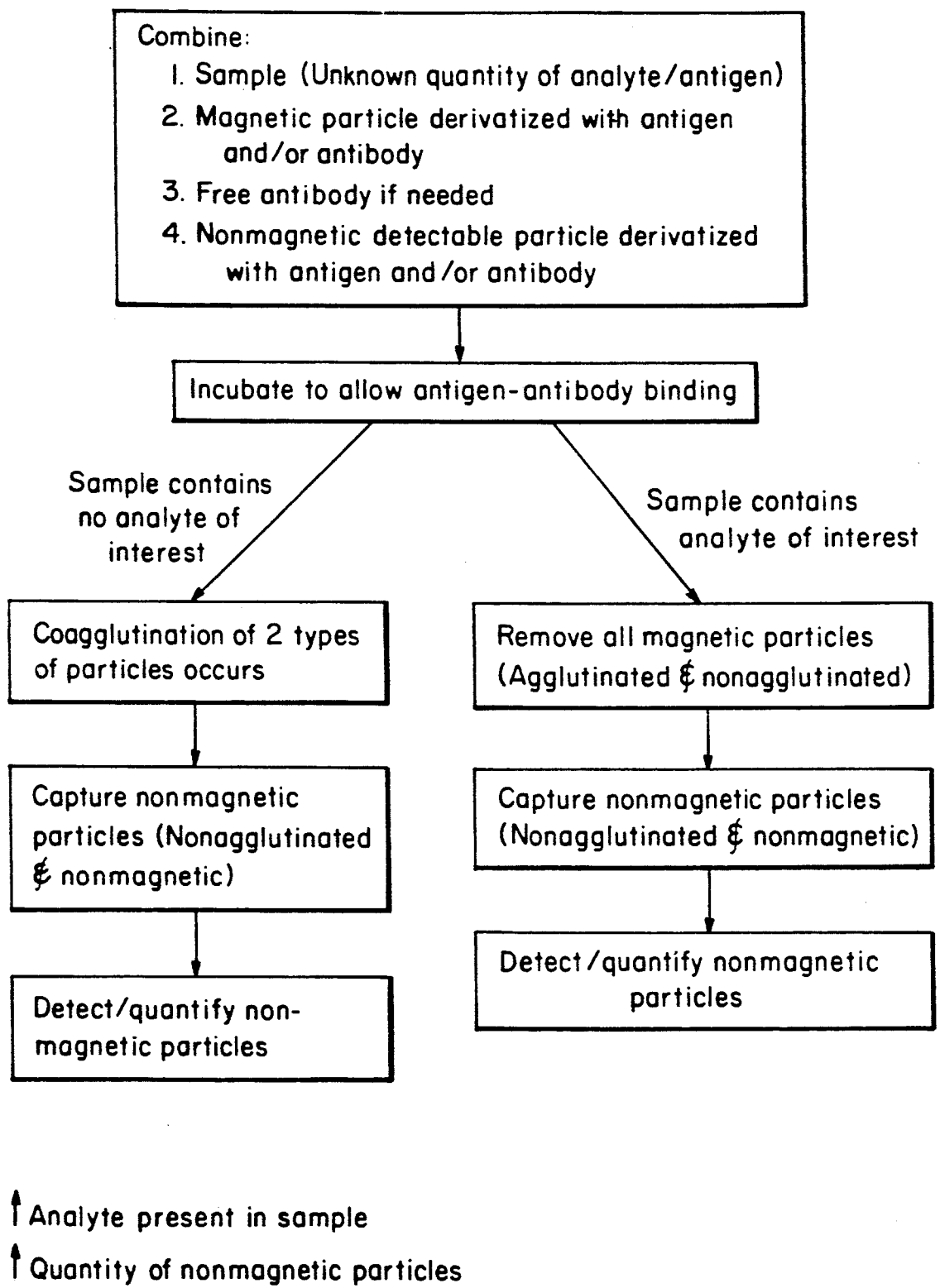
FIG. 1 is a schematic representation of the method of the present invention.

The present invention relates to a capillary flow device which is used for double capture assay procedures, such as the double capture immunoassay method of the present invention. The capillary flow device is described in detail below, with specific reference to its use in the double capture immunoassay method of the present invention. Briefly, the device comprises a sample receptacle, a capillary track, a collecting means and, optionally, a concentrator and a liquid reservoir.

According to the method of the present invention, a ligand or analyte of interest, which can be any substance for which there is a specific binding partner, can be detected simply and efficiently through the use of two types of particles, one magnetic and the other nonmagnetic and detectable. Both types of particles have ligand and/or specific binding partner attached to their surfaces in such a manner that they are available to bind with, respectively, their specific binding partner or ligand. Materials attached or affixed to the surfaces of particles are referred to herein as particle bound or bound (e.g., particle-bound or bound ligand, particle-bound or bound antigen, etc.).

In the method of the present invention, a sample to be analyzed for one or more analyte(s) of interest is combined with magnetic particles and nonmagnetic detectable particles bearing (i.e., having affixed to their surfaces) analyte of interest and/or specific binding partner for the analyte(s) of interest, free specific binding partner if needed, and any necessary buffers, salts and other reagents (e.g., proteins, detergents, synthetic and semi-synthetic polymers). The effects on agglutination when analyte of interest is present (e.g., when a liquid sample containing analyte against which the attached binding partner is specific is analyzed), are summarized in Table 1.

The method of the present invention will now be described in detail, with specific reference to its use as a double capture immunoassay. That is, it will be described in terms of determination (i.e., detection, identification, quantitation and/or isolation) of an analyte of interest which is an antigen or an antibody. It is to be understood, however, that the analyte of interest can be any ligand for which there is a specific binding partner. It is also to be understood that although the following description refers to determination of a single analyte of interest in a sample, the method of the present invention can be used to detect two or more analytes of interest at the same time.

Four possible schemes by which an analyte of interest which is an antigen or antibody can be determined according to the method of the present invention are represented in Table 1. Each is discussed below.

TABLE 1

| | Components of Immunoassay Procedure | | | Outcome if analyte present | |
|---|---|---|---|---|---|
| Analyte of interest | Attached to magnetic particles | Attached to non-magnetic detectable particles | Added anti-body | Inhibition of agglu-tination | Detectable particle at con-centrator |
| Antigen | Antigen | Antigen | Yes | Yes | Yes |
| Antigen | Antigen* | Antibody | No | Yes | Yes |
| Poly-valent Antigen | Antibody | Antibody | No | No | No |
| Antibody | Antigen | Antigen | No | No | No |

*Antigen can be attached to nonmagnetic detectable particles and antibody to magnetic particles In the first case represented in Table 1, in which an antigen is to be determined in a sample, the method of the present invention is carried out as follows and as represented in FIG. 1. The sample, magnetic particles bearing antigen of interest, nonmagnetic detectable particles bearing antigen of interest, (bound antigen of interest) free (unbound) antibody specific for the antigen of interest and any necessary buffers, salts and additional reagents are combined, to produce a reaction mixture.

After incubation for sufficient time and under appropriate conditions (e.g., application of sufficient energy to cause the particles to move so that they collide), interaction (binding) occurs between antigen of interest (bound and free) and its specific antibody, to produce what is referred to as a reacted mixture. If antigen of interest is present in the sample, it interferes with (inhibits) binding of free antibody and bound antigen of interest. This results in partial or complete inhibition of agglutination of particles present in the sample.

The reacted mixture is then subjected to a magnetic force of sufficient strength to capture essentially all magnetic particles and those nonmagnetic particles with which they are agglutinated as a result of antigen-antibody binding. At this point, the reacted mixture includes nonmagnetic nonagglutinated particles. The reacted mixture is subsequently analyzed for the presence or absence and/or quantity of nonmagnetic detectable (e.g., colored) particles. In one embodiment, this is carried out by bringing the reacted mixture into contact with a solid porous material, in which the pores are smaller than the particles. In general, the surface area of the solid porous material will be small, relative to the volume of particles and reacted mixture. The result is that the liquid passes through the porous material and the nonmagnetic detectable particles accumulate at its surface. This component serves as, and is referred to as, a particle concentrator. The presence or absence and/or quantity of nonmagnetic detectable particles is detected using known methods (e.g., by visual assessment of whether color is present at the porous material or not and, if present, its intensity).

Specifically, the extent to which the antigen of interest is present is reflected in the extent to which agglutination occurs, which is determined as follows: The combination of sample, magnetic particles and nonmagnetic detectable particles is maintained for sufficient time, under appropriate conditions, for binding of antigen and its specific antibody, to produce a reacted mixture which includes some or all of the following: unbound magnetic particles, complexes of one or more magnetic particle(s) and one or more nonmagnetic detectable particle(s), unbound nonmagnetic particles, magnetic particles bound to the antigen of interest present in the sample and nonmagnetic detectable particles bound to the antigen of interest present in the sample. The magnetic particles (agglutinated and nonagglutinated) are removed by magnetic attraction (e.g., by exposing the reacted mixture to a permanent magnet or electromagnet of sufficient strength to attract the magnetic particles). As represented in FIG. 1, this results in removal of both agglutinated and nonagglutinated magnetic particles from the sample. The reacted mixture is subsequently brought into contact with a solid support, which will generally be porous. As a result, the nonmagnetic, detectable particles, which are all nonagglutinated, are separated or removed from the sample and concentrated on the solid phase. As described above, the particles are detected (e.g., in the case of colored particles, simply by noting the presence of color at the particle concentrator). This demonstrates presence or absence of the analyte/antigen of interest. If antigen of interest is not present in the sample, free antibody binds with bound antigen of interest, resulting in agglutination of magnetic particles and nonmagnetic particles. Removal by application of magnetic force of magnetic particles also results in removal of nonmagnetic particles. As a result, no free particles are present in the collecting means, as evidenced by a lack of color change. If the antigen of interest is present in the sample, it interferes with binding of free antibody with bound antigen of interest. After removal of magnetic particles, with co-agglutinated nonmagnetic particles, the remaining nonmagnetic particles appear in the collecting means, as evidenced by the appearance of color. The extent to which color appears at the collecting means will be indicative of (related to) the amount of antigen of interest in the sample. The quantity of analyte/antigen of interest is determined by relating or comparing the number of nonmagnetic particles on the solid phase (i.e., captured nonmagnetic detectable particles) to a predetermined quantitative relationship between the number or volume of nonmagnetic particles and the quantity of analyte/antigen of interest.

In the second case represented in Table 1, in which a sample is to be assayed for an analyte/antigen of interest, the method of the present invention is carried out as follows: The sample is combined with magnetic particles having the antigen of interest affixed to their surfaces, nonmagnetic detectable particles having antibody specific for the antigen of interest attached to their surfaces, and any necessary buffers, salts and additional reagents, under conditions sufficient for binding of antigen of interest and its specific antibody. Specific antibody used must be bivalent or polyvalent. Two outcomes are possible. First, in the case in which the sample does not contain the analyte/antigen of interest, coagglutination of the two types of particles will occur. Upon exposure to a magnetic source, all of the magnetic particles will be removed; some of the magnetic particles are nonagglutinated and the remainder are agglutinated particles (resulting from antigen of interest-antibody interactions). Passage of the reacted mixture to the particle concentrator subsequently occurs. Only those nonmagnetic detectable particles not bound to magnetic particles (and previously removed) will be captured at the concentrator. In this case, in which the sample does not contain the analyte of interest, few, if any, particles will be captured on the concentrator.

Second, in the case in which the sample being tested does contain the analyte/antigen of interest, coagglutination of the two types of particles is interfered with or inhibited. Here, too, upon exposure to a magnetic source, the magnetic particles, both agglutinated and nonagglutinated, are removed. However, because of the interfering effect of the analyte/antigen of interest, fewer of the magnetic or nonmagnetic particles will be coagglutinated than is the case if the sample contains no analyte/antigen of interest. Nonmagnetic detectable particles will subsequently be captured at the particle concentrator. Because of the interfering effect of the analyte/antigen of interest, a larger percentage of the nonmagnetic detectable particles will appear at and be captured on the particle concentrator than is the case if the sample contains no analyte/antigen of interest. In the case in which the detectable particles are colored, the extent to which color appears at the particle concentrator will be indicative of the amount of analyte/antigen of interest. The quantity of analyte/antigen of interest is determined, as described above, by reference to a standard curve relating quantity of analyte/antigen of interest and the number of captured nonmagnetic particles.

In the third case represented in Table 1, in which a sample is to be assayed for an analyte/antigen of interest, the method of the present invention is carried out as follows: The sample is combined with magnetic particles having antibody specific for the antigen of interest affixed to their surfaces, nonmagnetic detectable particles having antibody specific for the antigen of interest affixed to their surfaces and any necessary buffers, salts and additional reagents, for sufficient time and under conditions sufficient for binding of antigen of interest and its specific antibody. Specific antibody used in this embodiment can be monovalent, bivalent or polyvalent and preferably will be bivalent or polyvalent in order for sufficient agglutination to occur.

After antigen of interest and specific antibody have interacted (resulting in production of a reacted mixture), and exposure to a magnet as described above has been carried out, the remaining reacted mixture (which includes nonmagnetic detectable particles) is brought into contact with a particle concentrator. If antigen of interest is present in the sample, agglutination of magnetic particles with nonmagnetic detectable particles occurs. As a result, nonmagnetic detectable particles are removed with the magnetic particles to which they are bound. Little, if any, detectable color change occurs at the particle concentrator. Alternatively, if antigen of interest is not present in the sample, agglutination of the two types of particles does not occur. As a result, magnetic particles are removed initially, followed by capture of nonmagnetic detectable particles at the particle concentrator. Presence or absence and/or quantity of the detectable particles at the concentrator is determined (e.g., visually if colored particles are used). As described above, quantitation is possible by relating or comparing the number or volume of captured detectable particles to a predetermined quantitative relationship between the number or volume of nonmagnetic particles and the quantity of antigen of interest.

In the fourth case represented in Table 1, in which a sample is to be assayed for an analyte/antibody of interest, the method of the present invention is carried out as follows: The sample is combined with magnetic particles bearing antigen for which the antibody of interest is specific, nonmagnetic detectable particles also bearing antigen for which the antibody of interest is specific and any necessary buffers, salts and additional reagents, for sufficient time and under conditions sufficient for binding of antibody of interest and antigen for which it is specific.

After antigen and antibody bind, the reacted mixture is exposed to a magnet which removes magnetic particles (as well as nonmagnetic divalent particles agglutinated with the magnetic particles). Nonmagnetic detectable particles are then detected (e.g., presence/absence, quantity, etc.). If antibody of interest is present in the sample, agglutination of the two types of particles occurs and, as a result, color change at the particle concentrator is less than is observed if no antibody of interest is prepared in the sample (i.e., agglutination increases as the concentration of antibody of interest increases). Quantitation of the antibody of interest is carried out by relating the number or volume of captured nonmagnetic detectable particles to a predetermined quantitative relationship between the number or volume of nonmagnetic particles and the quantity of antibody of interest.

Figure 2A:
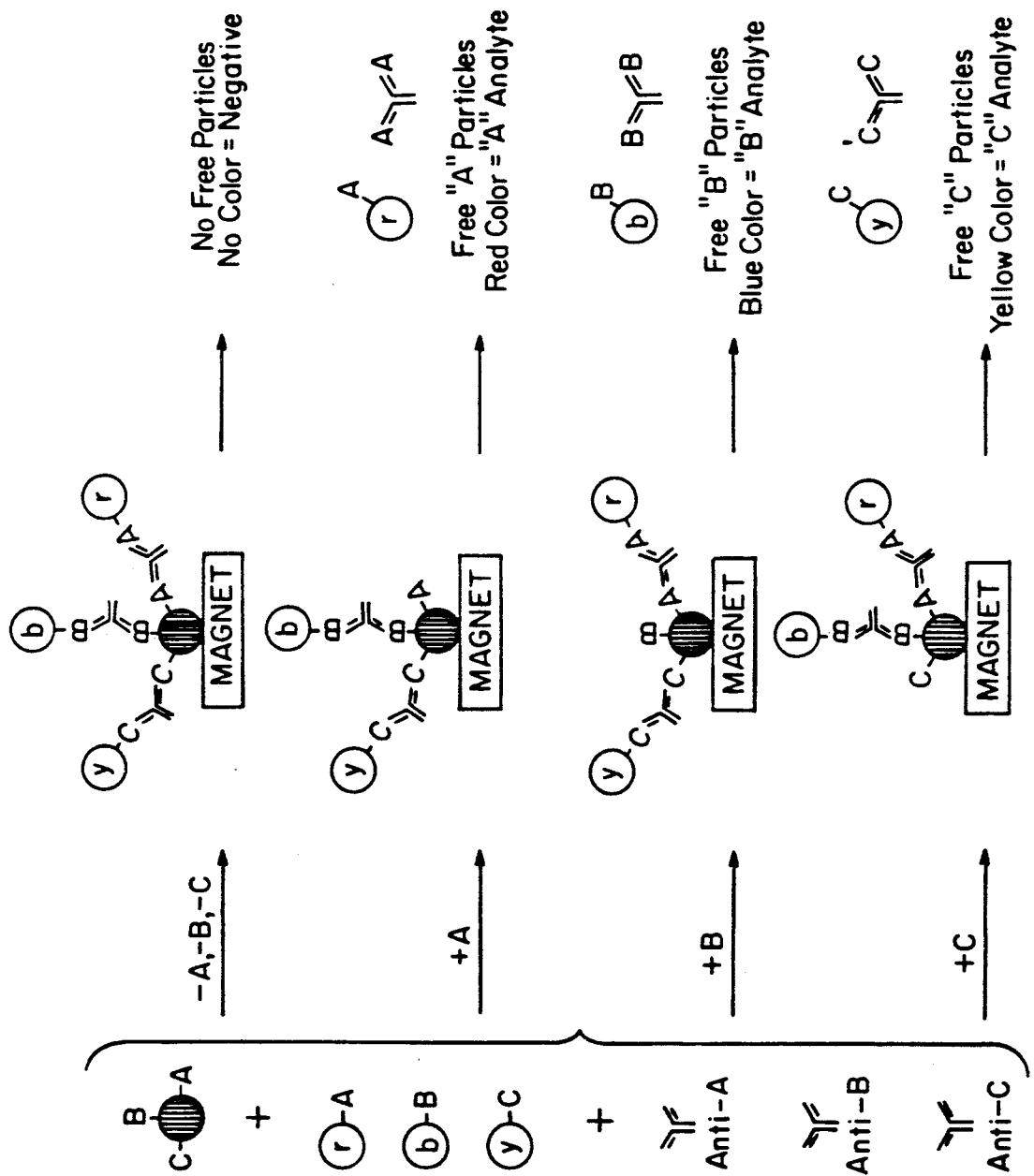
FIG. 2A is a schematic representation of determination of three analytes of interest by means of the method of the present invention.

As explained previously, more than one analyte of interest can be determined in a sample by means of the method of the present invention. Determination of three analytes of interest (e.g., antigens A, B and C) is represented in FIG. 2A. In this embodiment, magnetic particles to which all three analytes of interest are affixed, three different colored nonmagnetic particles, (each having affixed to its surface one of the three analytes (e.g., A, B or C), free specific binding partner for each analyte (e.g., anti-A, anti-B and anti-C) and any necessary buffers, salts, etc. are combined with the sample. If none of the analytes is present in the sample, agglutination of nonmagnetic and magnetic particles occurs as a result of antigen-antibody binding. In this case, no color change is observed at the collector or particle concentrator after the magnetic beads have been removed (taking with them the coagglutinated nonmagnetic detectable beads). As is also represented in FIG. 2A, if one of the three analytes (e.g., antigen A) is present in the sample, it interferes with agglutination of the magnetic particles with the nonmagnetic detectable particles bearing the same analyte (antigen A). As a result, the colored particles (e.g., red) bearing this analyte are not removed from the sample with the magnetic particles and a corresponding color change is evident at the collector or particle concentrator.

ANALYTES TO BE DETECTED

Any chemical or substance (analyte of interest) against which a specific binding partner antibody is available can be detected, identified, quantitated and/or isolated by use of the method of the present invention. For example, drugs and other haptens, proteins or portions thereof (oligopeptides, polypeptides), glycoproteins, lipoproteins, lipids, hormones can be determined according to the present method. In each application, a sample to be analyzed is combined, as described above, with magnetic particles and nonmagnetic detectable particles, which all bear appropriately selected antigen and/or antibody, free antibody where required and other components. The resulting combination is maintained under appropriate conditions and for sufficient time for antigen-antibody interaction to occur, to produce a reaction mixture. The reacted mixture is exposed to a magnetic source (to capture magnetic particles, alone and/or coagglutinated with nonmagnetic detectable particles) and subsequently brought in contact with a particle concentrator (to capture the nonmagnetic detectable particles).

The present method can be used as a screening technique, if desired. That is, it can be used to detect easily (e.g., by the presence or absence of nonmagnetic detectable particles at the particle concentrator) whether any analyte of interest is present in a sample or not.

In addition, the present method can be used to identify an analyte of interest. This is accomplished by combining the sample to be analyzed with magnetic particles to which the analyte (antigen) of interest is affixed, with nonmagnetic detectable particles to which antibody of defined specificity are affixed, free antibody if necessary and any other needed buffers, salts, etc. Appearance of the nonmagnetic detectable particles at the particle concentrator provides a means of identifying the analyte of interest.

The present method can also be used to quantitate analyte of interest in a sample. This can be carried out, for example, by combining the sample with magnetic particles bearing the analyte of interest and nonmagnetic detectable particles bearing antibody specific for the analyte and separating magnetic from nonmagnetic detectable particles, as described above. The number of detectable particles at the particle concentrator is then related to a standard, or predetermined quantitative relationship between the number of nonmagnetic particles and the quantity of analyte of interest (referred to as a standard or standard curve).

In the embodiment in which colored latex particles are used, for example, the standard can be constructed by establishing the relationship between the intensity of color generated (e.g., in the collecting means or at the particle concentrator) by a known number of particles) and the number of particles produced by an inhibition reaction of a known quantity of ligand.

Similarly, in those cases in which the nonmagnetic particles have antibody attached to them, the method of the present invention can be used to isolate an analyte of interest. This is accomplished by treating a sample, from which the analyte is to be isolated, as described above. Particles present at the particle concentrator will have attached thereto the analyte of interest. These particles can be separated from the rest of the sample and the analyte of interest removed from the particles, if desired, using known techniques.

The present method can be used to detect, identify, quantitate and/or isolate one or more analytes of interest in a sample. This is accomplished through the use of magnetic particles and nonmagnetic detectable particles which have one or more type(s) of ligand (e.g., antigen) and/or specific binding partner (e.g., antibody) affixed to their surfaces. One embodiment of the present method, in which three analytes are determined, is represented in FIG. 2A.

For example, if a sample is to be analyzed for three antigens of interest (a, b and c), magnetic latex particles derivatized with antigens a, b and c and nonmagnetic detectable latex particles bearing three different antibodies, each specific for one of the antigens on the magnetic particles, can be used. The nonmagnetic detectable latex particles must be distinguishable from one another (e.g., on the basis of colors). In this case, the sample is combined with both types of particles, as described above, and if any of the three antigens is present in the sample, agglutination of the nonmagnetic detectable latex particles with the respective magnetic particles will be inhibited. This inhibition will be detectable and can be quantitated through assessment of the number of detectable particles of each type (e.g., each color) at the particle concentrator.

Alternatively, a sample to be analyzed can be combined with a single population of magnetic latex particles derivatized with antigens a, b and c; a mixture of three distinguishable (e.g., different colored) nonmagnetic detectable particles also derivatized, respectively, with antigens a, b and c; a mixture of antibodies specific, respectively, for antigen a, b or c; and any necessary buffers, salts and other cofactors. If any of the three antigens is present in the sample, agglutination of the respective nonmagnetic detectable latex with the corresponding magnetic latex particles will be inhibited. After removal of the magnetic particles, nonmagnetic detectable particles whose agglutination with magnetic particles has been inhibited by antigen in the sample are detected (e.g., by detecting an appearance of color in the collector or at the particle concentrator of the device of the present invention). At that point, they can be detected and/or quantitated and presence/absence and/or quantity of analyte of interest can be determined.

MAGNETIC AND NONMAGNETIC DETECTABLE PARTICLES

As described previously, the method of the present invention relies on the use of two types of particles: magnetic particles and nonmagnetic detectable particles. The particles to which antigens or antibodies are attached can be of essentially any shape, although they will generally be microspheres. They can be made of essentially any insoluble material to which an antigen or an antibody can be attached or affixed in such a manner that they are not dislodged or become detached during the assay procedure. The material of which the particles are made must be reactive with ligand (e.g., antigen and/or antibody) and/or specific binding partner, or must have on its surface a material which can serve the purpose of affixing the desired reagents (e.g., antigen(s) or antibody(ies)) to particle surfaces.

Particularly useful for the nonmagnetic detectable particles used in the method are commercially-available latex (e.g., polystyrene, acrolein particles) particles which are about 0.1 micrometers to 10 micrometers in diameter. Particles of other materials, such as dextran, cellulose, red blood cells, glass, charcoal, and bentonite can also be used. In fact, any material which has reproducible agglutination properties and properties which aid in detection and to which antigens and/or antibodies can be attached is suitable for particles to be used in the method. Particularly useful for detecting the degree of particle agglutination are colored latex particles. The color present after magnetic particles have been removed will depend on the presence of a particle of a particular color (e.g., of particles bearing an antibody specific for the analyte/antigen of interest in the sample) in the sample (e.g., in the collector or at the particle concentrator of the capillary flow device). The intensity of the color depends on the extent to which such particles are present. Latex or other particles of more than one color (or other identifiable characteristic), each with a different analyte of interest or specific binding partner attached, can be used in the method of the present invention.

Any particle which responds to a magnetic field (and is not itself a magnet) and to which analyte of interest (ligand) and/or specific binding partner can be affixed can be used in the present method. For example, latex particles which are magnetized by $Fe_3O_4$ incorporation are useful. Other magnetized or magnetizable particles which can be used include those described by Odstrchel and co-workers. Odstrchel, T. H. et al., *Clinical Chemistry*, 29: 1242 (1983).

In each embodiment of the method of the present invention, the quantity of each type of particle used will be determined empirically. In general, however, sufficient magnetic particles are required such that the agglutinates formed during the reaction are sufficiently magnetically responsive that they can be removed from suspension. Sufficient nonmagnetic particles are needed to facilitate detection in the nonagglutinated state. Although the absolute number of each type of particle, as well as the ratio of particle types, will be determined empirically for each procedure and for each analyte of interest, in general, the concentration range for each particle type will not be greater than 10% by weight. The ratio of nonmagnetic to magnetic particles will generally be equal to or greater than 1.

LIGANDS AND/OR SPECIFIC BINDING PARTNERS

In the method of the present invention, particles have attached or affixed to their surfaces at least one analyte of interest (ligand, such as an antigen or an antibody) and/or at least one specific binding partner for the analyte of interest. For example, if a sample is to be assayed for antigen X, antigen X can be affixed to one type of particle (e.g., magnetic particles) and an antibody specific for antigen X can be bound to the second type of particle (e.g., nonmagnetic, detectable particles).

Attachment of ligand and specific binding partner (e.g., antigen and antibody) can be carried out in any manner which results in attachment to particles such that the ligand or specific binding partner (e.g., antigen or antibody) is not removed or dislodged during the assay procedure and such that it retains its function (e.g., ability to recognize and bind a corresponding antibody or antigen). For example, antigen or antibody can be affixed by passive adsorption, covalent attachment such as active ester linking, (see U.S. Pat. No. 4,045,384) or by being linked to/bound by a specific binding partner present on particle surfaces (e.g., by binding an antigen of interest to a particle by interaction with specific antibody on the particle surface). See also Bangs, L. B., *Uniform Latex Particles*, Seragen Diagnostics, Inc., P.O. Box 1210, Indiana, 46206 (1984).

For example, in the case in which a sample is to be tested for the presence of benzoylecgonine (cocaine), benzoylecgoneine is affixed to the surface of magnetic latex particles and to the surface of nonmagnetic detectable particles. The two types of benzoylecgonine-bearing particles are combined with free anti-benzoylecgonine monoclonal antibody (See Examplification). Upon combination with the sample, binding of the analyte in the sample with free antibody occurs, interfering with binding of particle-bound antigen and free antibody. The latex particles used can be colored, thus permitting their detection visually, following removal of all magnetic particles. In this way, agglutination and the extent to which it occurs (and, thus, the presence or absence and/or quantity of analyte of interest) can be detected easily.

Antigens and antibodies affixed to particles can be produced using standard techniques. Antigens used can be an entire protein or other substance or can be only the functional portion (i.e., that portion recognized by an antibody) of the protein (e.g., an oligopeptide or polypeptide) or other substances.

Antigens can be, for example, proteins, drugs, glycoproteins, haptens, carbohydrates, lipids, nucleic acids and hormones. They can be obtained, for example, by being extracted or removed from sources (e.g., blood, tissue) in which they occur naturally, by being produced chemically or using genetic engineering techniques, or by being synthesized mechanically.

Antibodies can also be produced using known techniques and can be monovalent, bivalent or polyvalent and/or monoclonal or polyclonal. The type of antibody used will be determined by the assay format. For example, in the case in which both magnetic and nonmagnetic detectable particles bear antigen of interest and specific unbound antibody is used, bivalent or polyvalent antibody is used in order to make it possible for the two types of particles to agglutinate.

DETECTION OF NONAGGLUTINATED NONMAGNETIC PARTICLES

The extent to which coagglutination of magnetic particles and nonmagnetic detectable particles occurs (or is inhibited) is determined by detecting the number or quantity of detectable particles in the reacted mixture after the magnetic particles are removed. Detection can be based on a distinguishing characteristic of the particles used. Such characteristics can be, for example, mass or size, color and ability to occlude light.

Particularly useful in assays carried out by the method of the present invention in which the presence of analyte of interest in a sample results in absence of particles in the collecting means or at the concentrator is the use of a dye or other coloring material to produce a reacted mixture which is a different color from the colored nonmagnetic particles used.

Figure 2B:
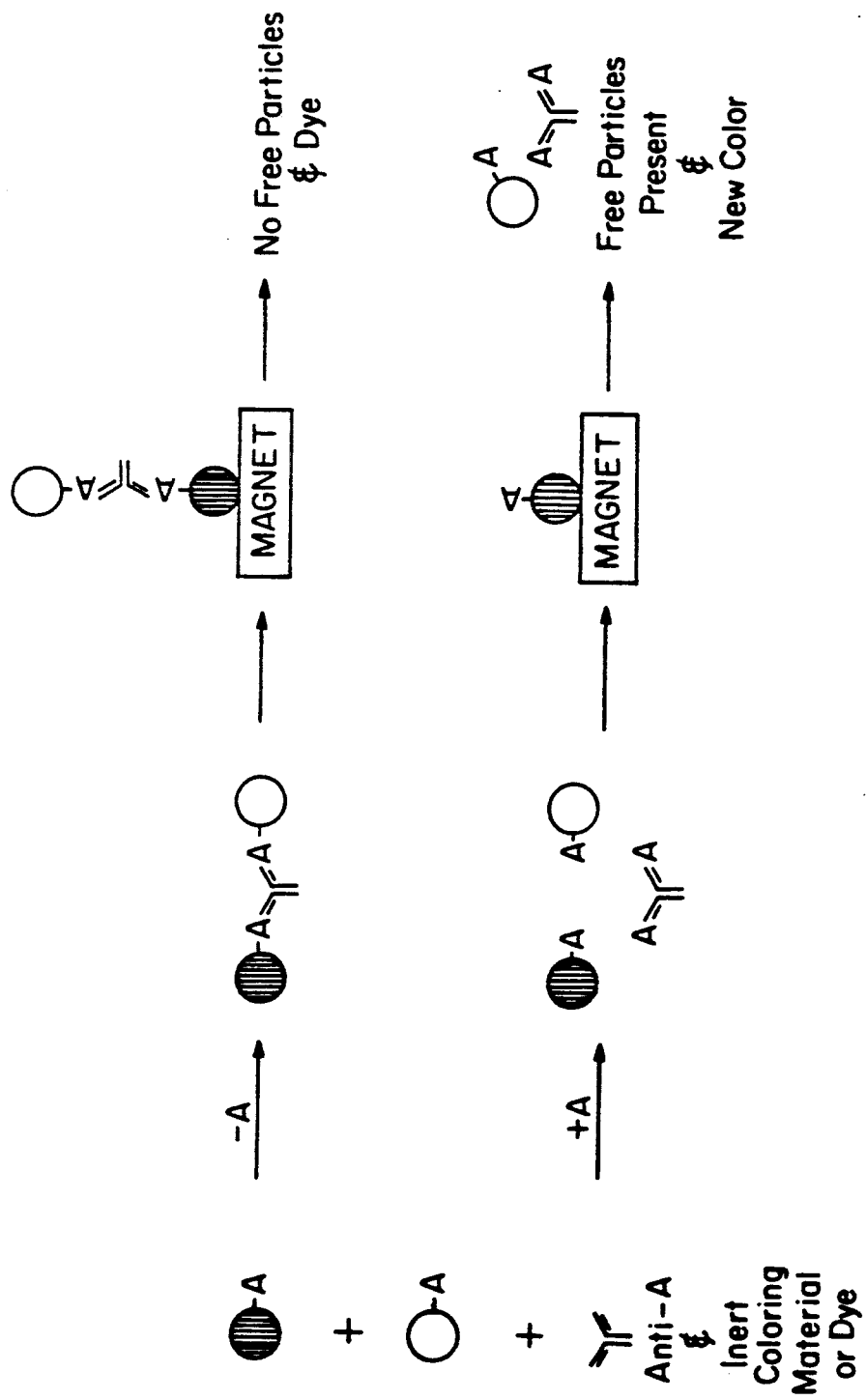
FIG. 2B is a schematic representation of an embodiment of the method in which an inert dye or coloring material is used.

For example, an inert dye or other coloring material which does not participate in analyte of interest-specific binding partner interaction is included in the reaction mixture. After removal of the magnetic particles, the dye in the reacted mixture will appear at and color a porous material used as the particle concentrator. If no particles are present at the concentrator, the only color present will be that of the dye. If particles are present at the concentrator, color due to the presence of dye and color due to the particles will be evident. That is, a third color, which is a combination of the two colors originally present (e.g., green, if two original colors were blue and yellow) will appear at the concentrator. Thus, the distinction will be made between two defined colors, rather than between presence or absence of color. This embodiment is represented schematically in FIG. 2B.

In addition, detectable particles modified with a specific enzyme and addition to the reacted mixture (after removal of magnetic particles) of the appropriate color-producing substrate is a useful detection means. Fluorescent or otherwise luminescent particles, which can be detected using known procedures and equipment, can also be used.

DOUBLE CAPTURE IMMUNOASSAY DEVICE

The method of the present invention can be carried out in any type of container or assay device suitable for introduction of the sample to be analyzed and reagents (e.g., magnetic particles, nonmagnetic detectable particles, free antibody, buffers, salts, other reagents), reaction of the sample and reagents, to produce a reacted mixture, and subsequent separation from the reacted mixture of the two types of particles. The receptacle can be used to receive added sample and reagents or, alternatively, can include reagents (e.g., lyophilized or otherwise preserved reagents), to which the desired amount of sample is added.

For this purpose, the assay device used includes a receptacle for the sample, magnetic particles, nonmagnetic detectable particles and other reagents; a means for passage of the resulting reacted mixture in proximity to a magnet; and a collecting means for the nonmagnetic detectable particles along with the reacted mixture or separated from the reacted mixture. The magnet can be affixed to the device or can be a separate magnet.

In a preferred embodiment, the combination of sample, particles and, optionally, additional reagents (free antibody, buffer, salts, etc.) flow from the sample receptable through a capillary means; this flow creates kinetic energy for the sample and reagents to collide and the agglutination reaction to occur, producing a reacted mixture. In this embodiment, after the reacted mixture has been exposed to a magnet to remove magnetic particles (agglutinated and nonagglutinated), it flows through the capillary means and comes into contact with a porous material which serves as a particle concentrator, thus making it possible to determine the extent to which agglutination has occurred.

Particularly useful for carrying out the method of the present invention is the capillary flow device of the present invention, which is described in detail in the following section.

CAPILLARY FLOW DEVICE

The capillary flow device of the instant invention comprises a sample receptacle connected to one end of a capillary track, the capillary track, through which the reaction mixture flows and a collecting means, for receiving the nonmagnetic detectable particles, either in the sample or separated therefrom, located at or close to the end of the capillary track opposite the sample receptacle. The device can additionally comprise a magnet, for separating magnetic from nonmagnetic particles, which is located between the sample receptacle and the collecting means. In a preferred embodiment, the capillary flow device includes the collecting means, which is a particle concentrator. The concentrator captures or collects the nonmagnetic detectable particles and removes the liquid portion of the reacted mixture, thus concentrating the detectable particles and facilitating detection. In one embodiment, a liquid reservoir is located adjacent to the particle concentrator, such that the particle concentrator is situated between the capillary track and the liquid reservoir. Such a capillary flow device is depicted in FIG. 3.

Figure 3:
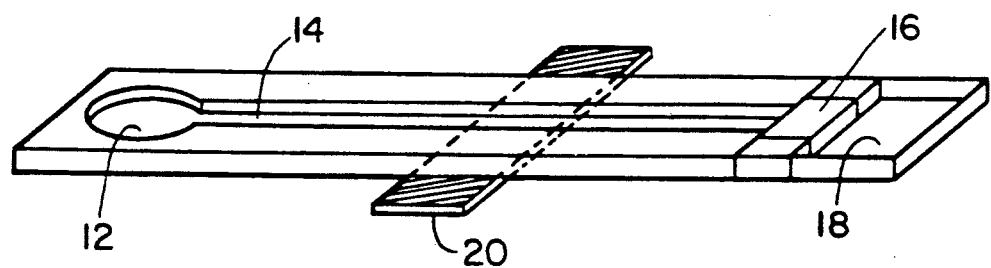
FIG. 3 is a view of the capillary flow device of the present invention.

In FIG. 3, the capillary flow device 10, is depicted as having the sample receptacle 12, the capillary track 14, the particle concentrator 16 and the liquid reservoir 18 in a substantially linear relationship. A magnet 20, is located adjacent to the capillary track 14, at a point between the sample receptacle 12 and the particle concentrator 16.

In practice, the sample receptacle receives a reaction mixture comprising a sample to be analyzed; magnetic particles and nonmagnetic detectable particles, both having bound thereto analyte of interest (e.g., antigen) and/or specific binding partner (e.g., antibody); free antibody, if required; and any necessary buffers, salts or cofactors. In one embodiment, components of the reaction mixture are preloaded in the sample receptacle or the initial part of the capillary track in a lyophilized or otherwise stabilized state. In a further embodiment, all components of the reaction mixture, except the sample to be analyzed, will be lyophilized or otherwise stabilized and placed within the sample receptacle or the initial capillary track section. The sample can then be added directly to the device to simultaneously rehydrate, mix and initiate the reaction.

In a particular embodiment, the reaction mixture in the capillary track comprises a biological sample, such as urine, a single population of magnetic latex particles derivatized with three antigens; a mixture of three differently colored latex particles, also derivatized with the three antigens, such that each color corresponds to a specific antigen; a mixture of antibodies to each of the three antigens; and any required buffers, salts or other cofactors.

After the components of the reaction mixture are present in the sample receptacle (e.g., by introducing all components or adding sample to lyophilized reagents present in the receptacle), the mixture begins to flow into the capillary track. This motion provides kinetic energy which allows the colored latex particles to agglutinate with the magnetic latex particles due to the action of the specific antibodies present in the reaction mixture. If any of the three antigens is present in the biological sample, the agglutination of the respective colored particles with the magnetic particles will be inhibited.

After a sufficient reaction and flow time, the reaction mixture encounters the field of a magnet located adjacent the capillary track. The magnet can be either a permanent magnet or an electromagnet and can be incorporated into the device or maintained in temporary proximity to the device. The effect of the magnetic field is to attract and hold the magnetic particles and nonmagnetic particles which are co-agglutinated, which are magnetically responsive because at least one component is a magnetic particle. If one of the antigens corresponding to one of the bound antibodies is present in the sample, its respective colored particle will be inhibited from coagglutination with the magnetic particles. In this case, the colored particle will not be attracted by the magnetic field and will pass through the magnetic field and continue traveling along the capillary track.

These nonagglutinated, colored particles continue along the capillary track until they encounter the particle concentrator and accumulate thereon. This results in a change of color at the particle concentrator surface, corresponding to the color of the nonagglutinated particles. The particular antigen present can be then identified by the particular color of the particle concentrator. The remainder of the reaction mixture will flow into the liquid reservoir. The particle concentrator is preferably a porous or semiporous, solid phase material. In one embodiment, the particle concentrator comprises filter paper.

The capillary flow device can be constructed in accordance with the methods of U.S. Pat. No. 4,596,695, the teachings of which are incorporated herein by reference. As described in U.S. Pat. No. 4,596,695, the device can be constructed of two panels, of which at least one will generally be a wettable material. The panels are bounded by a spacing means to define a narrow space, thereby providing the capillary track. The spacing means can comprise paint, silkscreening, ink, polyester film, dust, surface irregularities on the panels, or a discrete film. However, the invention is not intended to be limited to such spacing means. In one embodiment, each of the panels is glass. In one embodiment, each of the panels is a clear, colorless, polymeric material, such as acrylic resin. In a further embodiment, only one panel is clear and colorless; the other can be colored.

The gap between the upper and lower panels directly affects the capillary force within the device. As the gap distance decreases, the capillary force of the chamber and the resistance to flow increase. As the gap distances increases, the capillary force of the chamber decreases, as does the resistance to flow. Thus, by varying the gap between the panels, the speed of reacted mixture flow in the capillary track can be varied, thereby affecting the reaction time for agglutination. Thus, the capillary track can be designed to allow sufficient time for agglutination prior to encountering the magnetic field. Alternately, the position of the magnet can be varied such that the magnetic field is encountered at an earlier or later section of the capillary track, depending upon the particular agglutination reactions employed.

In a preferred embodiment of the device, at least one vent hole is provided for the liquid reservoir. This vent hole serves to prevent blockage of the flow of the reaction mixture, which results from air trapped within the capillary track or liquid reservoir, by providing an escape for the air pushed ahead of the reaction mixture. The vent hole also provides a means to reduce random evaporation that would occur if the liquid reservoir were more completely open and, thereby, provides an improved manner with which to control the end point of the reaction. Additionally, by providing a closed liquid reservoir with a vent hole, rather than an open reservoir, containment of the reaction mixture is greatly enhanced.

The particle concentrator, which serves to localize captured particles, can be either permanently contained within the device or can be removable. Any means by which the nonmagnetic particles remaining in the reacted mixture after it has been exposed to a magnetic force can be separated from the liquid portion of the sample being analyzed can serve as a particle concentrator. For example, a barrier, past which the liquid sample flows (leaving the nonmagnetic particles behind), can be used. Alternatively, any solid phase material having pores small enough to entrap the nonmagnetic detectable particles, yet large enough to allow efficient liquid flowthrough can be employed. Particularly useful are filter paper and cotton polyester filters. In a preferred embodiment, the material will possess properties which enhance detection of the trapped particles. For example, chemical attachment means via utilization of avidin-biotin interactions, ionic interactions or immunological interactions can be used to enhance particle capture on the particle concentrator. Additionally, these methods can be used to localize the captured particles, thereby enhancing interpretation of the sample results.

Particle detection can also be enhanced by providing particle formulations which allow different methods to detect agglutination inhibition. For example, the detector particles can be modified with specific enzymes used in conjuction with appropriate color-producing concentrator substrates. Alternately, the particles can be fluorescent or otherwise luminescent. In this embodiment, detection means capable of interpreting fluorescent or luminant properties are required.

The invention is not intended to be limited to the three antigen embodiment described previously. Rather, the invention can be used for a single analyte or for as many analytes for which distinctly colored particles are available. However, for identification of a large number of analytes within a sample, multiple devices, containing different agglutinating species are preferred.

In a further embodiment of the invention, multiple, parallel, capillary tracks are present on a single device. This would make it possible, through use of differing specific binding pairs, to detect simultaneously a larger number of analytes than would be possible using a single capillary track or particle concentrator. Alternately, such a parallel track configuration would allow a simple method for comparing like antigens in a plurality of samples or a method for studying the analyte content of a single sample over an extended period of time.

Figure 4:
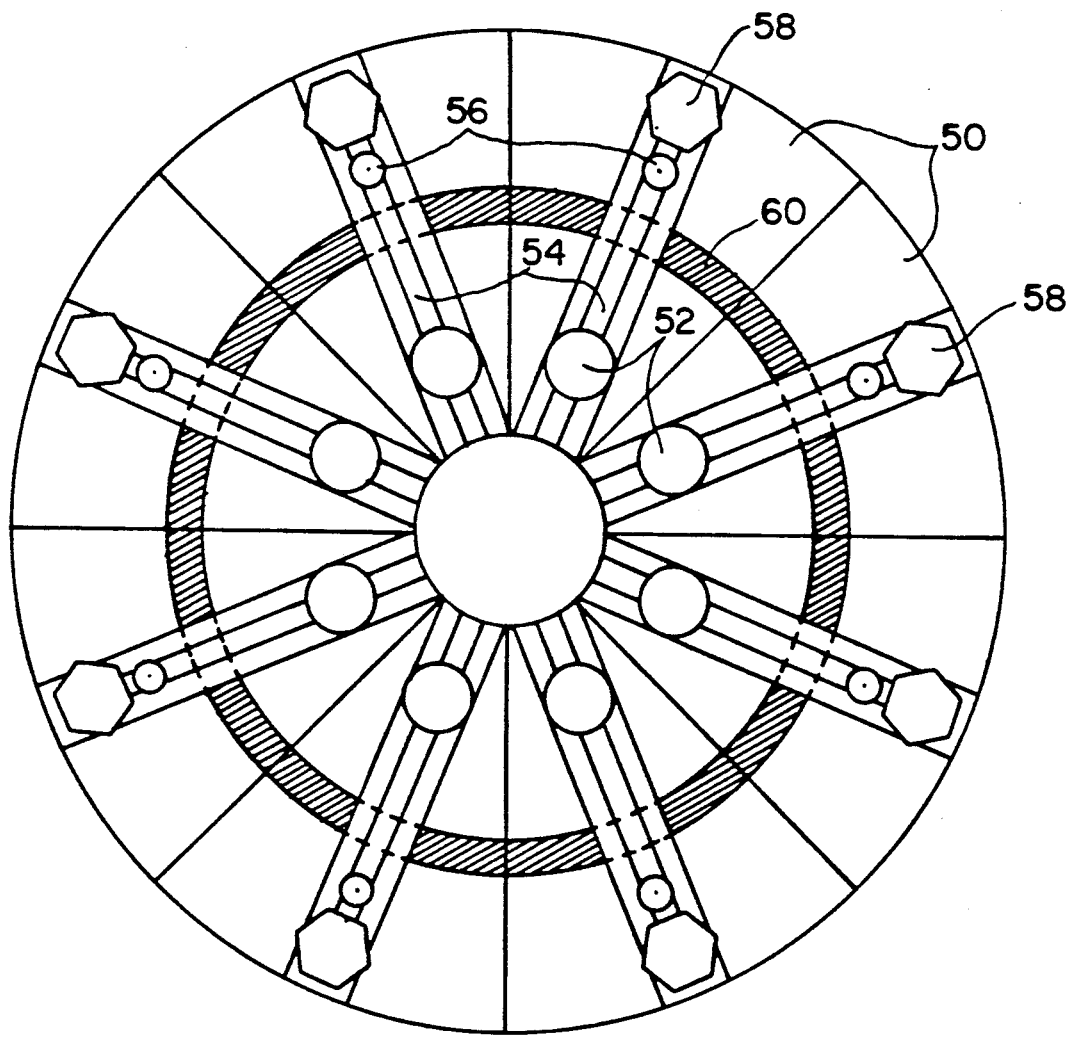
FIG. 4 is a top view of the multiple capillary flow device of the present invention.

A variation of the multiple capillary track device is presented in FIG. 4. In FIG. 4, a plurality of capillary flow devices 50, is maintained in a circular configuration. As in the case of the single track device 10 of FIG. 3, each unit 50 of FIG. 4 comprises a sample receptacle 52, a capillary track 54, a particle collector 56, and a liquid reservoir 58. A circular magnet 60, is maintained in close proximity to the capillary tracks 54. As before, the magnet can be either a permanent magnet or electromagnet and can be either permanently attached to the device or temporarily located in close proximity to the device. In another embodiment, the magnetic field can be produced by a plurality of individual magnets, such that at least one magnet is located in close proximity to each capillary track. This embodiment eliminates the need for a magnetic ring and reduces the total amount of magnetic material required. As with the linear multiple track device described previously, the circular device offers the ability to analyze a sample containing a large number of antigenic species, the ability to simultaneously analyze a plurality of samples, and the ability to cōmpare the amount of specific antigens present in a single sample over an extended period of time.

The apparatus of FIG. 4 also can allow the use of centrifugal force to affect the time required for the reaction mixture to travel the length of the capillary. For example, in the configuration of FIG. 4, wherein the sample receptacles are located closer to the center than are the particle collectors, rotation of the device would provide a centrifugal force which would increase the speed at which the reaction mixture traveled along each capillary track. Such rotation can be provided by placing the device upon a turntable. Alternately, if the device is configured with the particle concentrator located closer to the center than the sample receptacle, centrifugal force will act to inhibit the travel of the reaction mixture along the capillary track. Such a configuration would allow a greater time for agglutination to occur before the reaction mixture encountered the magnetic field and particle concentrator.

This invention will now be illustrated by the following Exemplification, which is not intended to be limiting in any way.

EXEMPLIFICATION

Determination of Benzoylecgonine Concentration in Urine

The following reagents and protocol are used to termine the concentration of benzoylecgonine (cocaine) in a urine sample.

Reagents (All percentages are expressed wt/vol.)

1. Reaction buffer. 1M Phosphate buffer, pH 5.6 containing 2% polyethylene glycol 8000, 1% polyvinylpyrrolidone 360, 0.1% azide and, optionally, 1% bovine serum albumin.
2. Antibody diluent. .05M Hepes (n-2-hydroxyethyl piperazine-N-2-ethane sulfonic acid), pH 6.0 containing 2.5 mg/ml bovine serum albumin, 0.1% azide.
3. Sample as pooled urine control containing standard amounts of benzoylecgonine, 0.1% azide.
4. Benzoylecgonine modified latex. 3% suspension in water, 0.1% azide.
5. Benzoylecgonine modified magnetic latex. 0.5% suspension in water, 0.1% azide.
6. Anti-benzoylecgonine monoclonal antibody in antibody diluent.

Protocol

1. Mix:
   30 ul reaction buffer
   10 ul sample (urine control)
   30 ul monoclonal anti-benzoylecgonine in antibody diluent
   30 ul benzoylecgonine latex
   30 ul magnetic benzoylecgonine latex
2. Add mixture to slide.

3. Allow to flow and agglutinate for one minute at room temperature.
4. Place slide in contact with permanent magnet.
5. Allow slide to flow until viewing window is filled.
6. Determine relative latex concentration in window (in thin film) by light scattering. This was carried out using a light scattering instrument (photodiode detector), at a 45° angle from an emitter of 875 nm.

Figure 5:
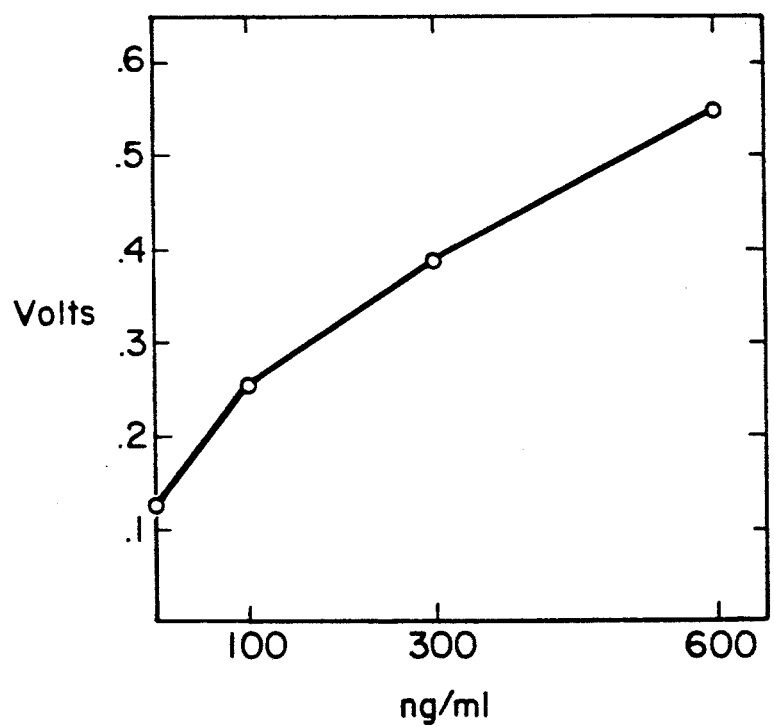
FIG. 5 is a graphic representation of the relationship between the concentration of benzoylecgonine in urine and light scattering as determined by a photodiode detector.

Results of such an analysis are presented in Table 2 and FIG. 5.

TABLE 2

| Determination of Benzoylecgonine Concentration | | |
|---|---|---|
| Sample | Benzoylecgonine Concentration | Light Scattering Reading (volts) |
| 1 | 0 ng/ml | 0.125 |
| 2 | 150 ng/ml | 0.255 |
| 3 | 300 ng/ml | 0.387 |
| 4 | 600 ng/ml | 0.549 |

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A double capture immunoassay for an antigen of interest in a sample, comprising the steps of:
   a. combining: 1) the sample; 2) magnetic particles having affixed thereto antigen of interest; 3) nonmagnetic detectable particles having affixed thereto the antigen of interest; and 4) unbound antibody specific for the antigen of interest, to produce a reaction mixture;
   b. incubating the reaction mixture under conditions and for a period of time sufficient for antigen of interest to bind to antibody specific for the antigen;
   c. separating the magnetic particles from the nonmagnetic particles;
   d. capturing the nonmagnetic particles on a solid material; and
   e. determining the presence or absence of captured nonmagnetic particles on the solid material.
   f. determining the presence or absence of the antigen of interest in the sample by relating the presence or absence of captured nonmagnetic particles to a relationship between captured nonmagnetic detectable particles having affixed thereto the antigen of interest and the antigen of interest.

2. A double capture immunoassay of claim 1 wherein the antigen of interest is quantitated by determining the number of captured nonmagnetic particles on the solid material and relating the number of captured nonmagnetic particles present on the solid material to a predetermined quantitative relationship between the number of captured nonmagnetic particles and the quantity of antigen of interest.

3. A double capture immunoassay for an antibody of interest in a sample, comprising the steps of:
   a. combining: 1) the sample; 2) magnetic particles having affixed thereto antigen for which the antibody of interest is specific; and 3) nonmagnetic detectable particles having affixed thereto antigen for which the antibody of interest is specific, to produce a reaction mixture;
   b. incubating the reaction mixture under conditions and for a period of time sufficient for antibody of interest to bind to antigen for which it is specific;
   c. separating the magnetic particles from the nonmagnetic particles;
   d. capturing the nonmagnetic particles on a solid material;
   e. determining the presence or absence of captured nonmagnetic particles on the solid material.
   f. determining the presence or absence of the antibody of interest in the sample by relating the presence or absence of captured nonmagnetic particles to a relationship between captured nonmagnetic detectable particles having affixed thereto the antigen for which the antibody of interest is specific and the antibody of interest.

4. A double capture immunoassay of claim 3 wherein the antibody of interest is quantitated by determining the number of captured nonmagnetic particles on the solid material and relating the number of captured nonmagnetic particles present on the solid material to a predetermined quantitative relationship between the number of captured nonmagnetic particles and the quantity of antibody of interest.

5. A double capture assay for a drug of abuse in a sample, comprising the steps of:
   a. combining: 1) the sample; 2) magnetic particles having affixed thereto the drug of abuse or a metabolite thereof; 3) nonmagnetic detectable particles having affixed thereto the drug of abuse or a metabolite thereof; and 4) specific binding partner for the drug of abuse or a metabolite thereof, to produce a reaction mixture;
   b. incubating the reaction mixture under conditions and for a period of time sufficient for the drug of abuse and the specific binding partner to bind;
   c. separating the magnetic particles from the nonmagnetic particles;
   d. capturing the nonmagnetic particles; and
   e. determining the presence or absence of captured particles.
   f. determining the presence or absence of the drug of abuse in the sample by relating the presence or absence of captured nonmagnetic particles to a relationship between captured nonmagnetic detectable particles having affixed thereto the drug of abuse or a metabolite thereof and the drug of abuse.

6. A double capture assay of claim 5 wherein the drug of abuse is cocaine, the metabolite thereof is benzoylecgonine, and the specific binding partner is monoclonal anti-benzoylecgonine.

7. An assay for detecting an analyte of interest which is a member of a specific binding pair in a sample, comprising the steps of:
   a) combining the following components:
      i) the sample;
      ii) magnetic particles having affixed thereto a first member of a specific binding pair;
      iii) non-magnetic detectable particles having affixed thereto a second member of a specific binding pair; and
   b) incubating the mixture from step a) under conditions appropriate for the binding of complementary members of a specific binding pairs;
   c) separating the magnetic particles, and non-magnetic particles bound thereto, from unbound non-magnetic particles;
   d) capturing the unbound non-magnetic particles; and e) determining the presence of captured unbound nonmagnetic particles.

f. determining the presence or absence of the analyte of interest in the sample by relating the presence or absence of captured nonmagnetic particles to a relationship between captured nonmagnetic detectable particles having affixed thereto the second member of the specific binding pair and the analyte of interest.

8. A method of claim 7 wherein steps b), c) and d) are carried out in a capillary flow device comprising:
a) a capillary track having a first and a second distal end;
b) a sample receptacle in communication with the first distal end of the capillary track; and
c) a liquid reservoir at the second distal end of the capillary track.

9. A method of claim 8 wherein the capillary flow device further comprises:
d) a particle concentrator in communication with the second distal end of the capillary track.

10. An assay of claim 7 wherein the amount of the analyte of interest present in the sample is quantitated by determining the number of captured unbound non-magnetic particles and relating the number of captured unbound non-magnetic particles to a predetermined quantitative relationship between the number of captured non-magnetic particles and the quantity of the analyte of interest.

11. An assay of claim 7 wherein the analyte of interest is an antigen specifically reactive with an antibody, the first member of a specific binding pair is an antigen specifically reactive with the antibody and the second member of a specific binding pair is the antibody.

12. An assay of claim 7 wherein the analyte of interest is an antigen specifically reactive with an antibody, the first member of a specific binding pair is the antibody and the second member of a specific binding pair is an antigen specifically reactive with the antibody.

13. An assay of claim 7 wherein the analyte of interest is an antigen, the first member of a specific binding pair is an antibody specifically reactive with the antigen and the second member of a specific binding pair is an antibody specifically reactive with the antigen.

14. An assay of claim 7 wherein the analyte of interest is an antibody and the first member of a specific binding pair is an antigen specifically reactive with the antibody and the second member of a specific binding pair is an antigen specifically reactive with the antibody.

15. An assay of claim 7 wherein the analyte of interest is an antibody and the first member of a specific binding pair is an antigen specifically reactive with the antibody and the second member of a specific binding pair is an antibody specifically reactive with the antigen.

16. An assay of claim 7 wherein the analyte of interest is an antibody specifically reactive with an antigen and the first member of a specific binding pair is an antibody specifically reactive with the antigen and the second member of a specific binding pair is the antigen.

17. An assay for detecting an analyte of interest which is a member of a specific binding pair in a sample, comprising the steps of:
a) combining the following components:
i) the sample;
ii) magnetic particles having affixed thereto a first member of a specific binding pair;
iii) non-magnetic detectable particles having affixed thereto a second member of a specific binding pair; and
iv) a third member of a specific binding pair specifically reactive with the analyte of interest; and b) incubating the mixture from step a) under conditions appropriate for binding of complementary members of specific binding pairs;

c) separating the magnetic particles, and non-magnetic particles bound thereto, from unbound non-magnetic particles;

d) capturing the unbound non-magnetic particles; and e) determining the presence of captured unbound nonmagnetic particles.

f. determining the presence or absence of the analyte of interest in the sample by relating the presence or absence of captured non-magnetic particles to a relationship between captured non-magnetic detectable particles having affixed thereto the second member of the specific binding pair and the analyte of interest.

18. A method of claim 17 wherein steps b), c) and d) are carried out in a capillary flow device comprising:
a) a capillary track having a first and a second distal end;
b) a sample receptacle in communication with the first distal end of the capillary track; and
c) a liquid reservoir at the second distal end of the capillary track.

19. A method of claim 18 wherein the capillary flow device further comprises:
d) a particle concentrator in communication with the second distal end of the capillary track.

20. An assay of claim 17 wherein the amount of the analyte of interest present in the sample is quantitated by determining the number of captured unbound non-magnetic particles and relating the number of captured unbound non-magnetic particles to a predetermined quantitative relationship between the number of captured non-magnetic particles and the quantity of the analyte of interest.

21. An assay of claim 17 wherein the analyte of interest is an antigen reactive with an antibody, the first member of a specific binding pair is an antigen specifically reactive with the antibody, the second member of a specific binding pair is antigen specifically reactive with the antibody and the third member of a specific binding pair is the antibody.

22. An assay of claim 17 wherein the analyte of interest is an antibody specifically reactive with an antigen, the first member of a specific binding pair is an antibody specifically reactive with the antigen, the second member of a specific binding pair is an antibody specifically reactive with the antigen, and the third member of a specific binding pair is the antigen.

23. An assay of claim 17 wherein the analyte of interest is an antigen, the first member of a specific binding pair is an antibody specifically reactive with the antigen, the second member of a specific binding pair is an antibody specifically reactive with the antigen and the third member of a specific binding pair is an antigen specifically reactive with the first member of a specific binding pair and the second member of a specific binding pair.

* * * * *